United States Patent [19]

Tosaki

[11] Patent Number: 4,584,882

[45] Date of Patent: Apr. 29, 1986

[54] DYNAMIC VISCOELASTICITY MEASURING APPARATUS OF TORSIONAL VIBRATION TYPE

[75] Inventor: Chikao Tosaki, Kawasaki, Japan

[73] Assignee: Japan Synthetic Rubber Co., Ltd., Tokyo, Japan

[21] Appl. No.: 654,024

[22] Filed: Sep. 24, 1984

Related U.S. Application Data

[63] Continuation-in-part of Ser. No. 293,666, Aug. 17, 1981.

[30] Foreign Application Priority Data

Sep. 20, 1980 [JP] Japan .................. 55-131141

[51] Int. Cl.$^4$ .......................................... G01N 29/00
[52] U.S. Cl. .................................... 73/847; 374/53
[58] Field of Search .................... 73/60, 590, 847; 374/53, 48

[56] References Cited

U.S. PATENT DOCUMENTS

| | | | |
|---|---|---|---|
| 3,447,365 | 6/1969 | Lloyd et al. | 73/814 |
| 3,488,992 | 1/1970 | Veith et al. | 374/48 |
| 3,554,003 | 1/1971 | Wise | 374/48 |
| 3,681,980 | 8/1972 | Decker | 73/794 |
| 4,468,953 | 9/1984 | Garritano | 73/60 |

FOREIGN PATENT DOCUMENTS

| | | | |
|---|---|---|---|
| 193779 | 3/1967 | U.S.S.R. | 73/60 |
| 0976349 | 11/1982 | U.S.S.R. | 73/60 |

*Primary Examiner*—Anthony V. Ciarlante
*Attorney, Agent, or Firm*—Oblon, Fisher, Spivak, McClelland & Maier

[57] ABSTRACT

A dynamic viscoelasticity measuring apparatus of torsional vibration type comprising a driving portion for converting a rotary movement to a rotary vibratory movement having a driving shaft having an eccentric end for rotation at an isometric velocity, a driven shaft supported at a right angle to said driving shaft for rotation, an intermediate arm revolving along the side of a cone having a top at the point of intersection of the center line of said driving shaft and the center line of said driven shaft disposed at right angles to each other and a bottom at a circle described by the eccentric end of the driving shaft, and connecting means for operatively connecting opposite ends of said intermediate arm to said driven shaft and said driving shaft and a driving dice for imparting vibration to a specimen, dynamic viscoelasticity of which is to be measured, through said swinging shaft, said vibration having an approximately sinusoidal waveform with complete symmetry.

12 Claims, 22 Drawing Figures

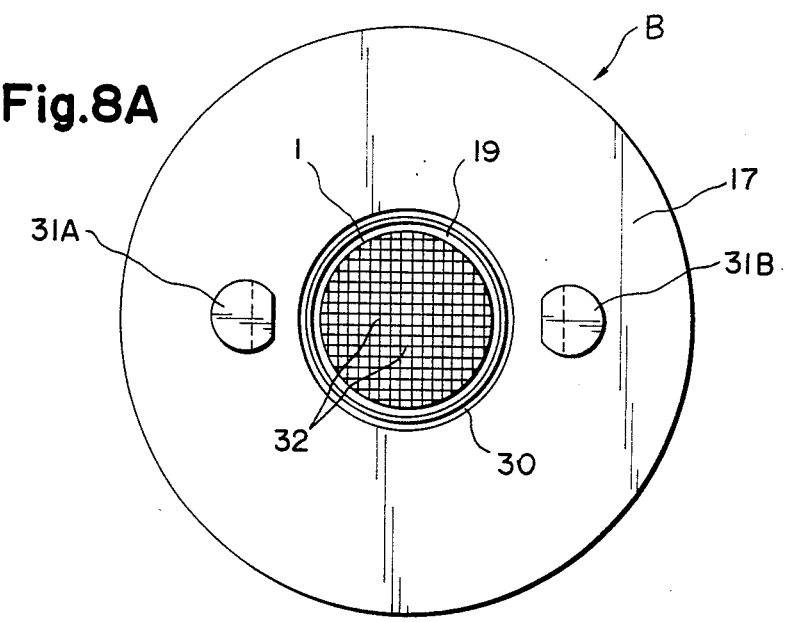
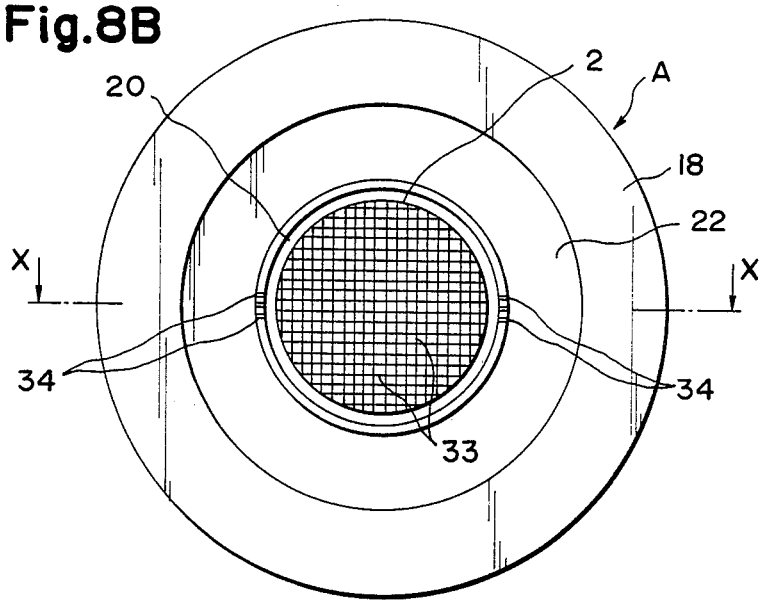
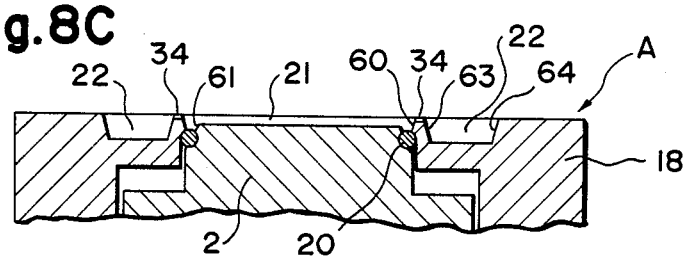

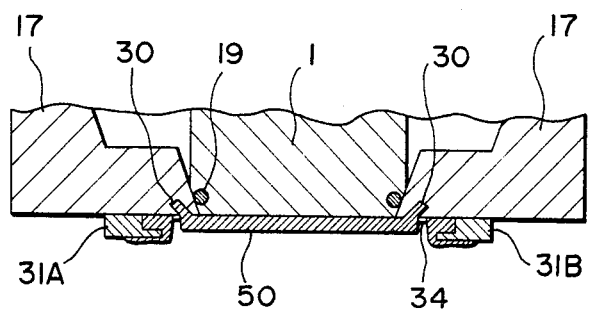
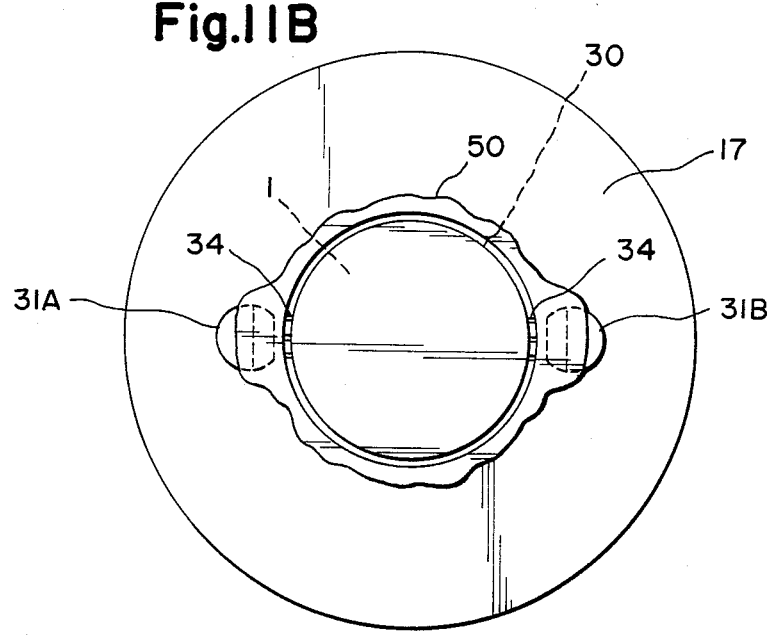

DYNAMIC VISCOELASTICITY MEASURING APPARATUS OF TORSIONAL VIBRATION TYPE

This application is a continuation-in-part of U.S. Ser. No. 293,666, filed Aug. 17, 1981.

BACKGROUND OF THE INVENTION

1. Field of the Invention

The present invention relates to a dynamic viscoelasticity measuring apparatus and more particularly to an enclosed type dynamic viscoelasticity measuring apparatus of torsional vibration type in which a pair of dices disposed in opposed relationship define a specimen chamber and one dice is imparted with rotary vibration of a predetermined amplitude so that a torque transmitted to the other dice is detected.

2. Description of the Prior Art

A dynamic viscoelasticity measuring apparatus of torsional vibration type (referred to as dynamic viscoelasticity measuring apparatus hereinafter) is an apparatus for detecting a change of viscoelastic properties (referred to as cure rate) while a viscoelastic material is being cured. Such an apparatus is used to determine whether or not a viscoelastic material such as unvulcanized rubber or uncured thermoset (referred to as specimen, hereinafter) has predetermined physical properties after vulcanization or curing. Such apparatus as described above is disclosed in, for instance, U.S. Pat. No. 3,488,992 or Japanese Patent Application Laying-open No. 53-144,794. Such apparatus measures a change of cure rate of specimen with time while heating it, thereby automatically recording a so-called curing curve. Important physical properties of the specimen can be obtained by analyzing the thus obtained curing curve. It can be also determined that a number of specimens have the same physical properties by confirming that substantially the same curing curve is obtained for a number of specimens.

FIG. 1A shows, for instance, a viscoelasticity measuring apparatus as disclosed in Japanese Patent Application Laying-open No. 53-144,794. Reference numeral 1 denotes a detection dice disposed on the detection side and reference numeral 2 is a driving dice disposed in opposed relationship with the detection dice 1. The detection dice 1 is securely mounted on a torque detection shaft 3, while the driving dice 2 is securely mounted on a vibration shaft 4.

The vibration shaft 4 is pivotably mounted on a lower base 5 and has a lower end connected through crank arms 6 and an eccentric shaft 7 to a motor 8 so that periodic vibrations may be imparted to the vibration dice 2.

The detection shaft 3 is pivotably fixed to an upper base 9 and a torque sensing load cell 11 is attached to one end of a torque arm 10, the other end of which is securely fitted to the upper end of the detection shaft 3. An air cylinder 12 is provided so as to move the upper base 9 vertically.

Reference numerals 13 and 14 are heating plates mounted through insulating members 15 and 16 to the upper and lower bases 9 and 5, respectively. Reference numerals 17 and 18 are stationary dices fixed to the heat plates 13 and 14, respectively. A ring-shaped packing 19 is interposed between the stationary dice 17 and the detection dice 1, while a ring-shaped packing 20 is interposed between the stationary dice 18 and the driving dice 2, so that a specimen is prevented from leaking from a specimen chamber 21 which is tightly defined between the detection and driving dices 1 and 2.

Reference numeral 22 is a groove formed around the periphery of the specimen chamber 21 so that the overflow flash of the specimen charged into the specimen chamber 21 can be received in this groove 22. Reference numerals 23A, 23B, 24 and 25 are heaters disposed adjacent to the dices 1 and 2.

In the viscoelasticity measuring apparatus of the type described, the upper base 9 is lifted by the air cylinder 12 so that the detection and driving dices 1 and 2 are moved away from each other. A specimen is placed upon the driving dice 2 and then the upper base 9 is lowered so that the rubber specimen is enclosed in the specimen chamber 21 which is tightly defined between the dices 1 and 17 and the dices 2 and 18. Thereafter, while the specimen is maintained at a predetermined temperature by the heaters 23A, 23B, 24 and 25, the driving dice 2 is reciprocated by the driving mechanism. The motion of the driving dice 2 is transmitted to the specimen and a torque which is transmitted from the specimen through the detection dice 1 and the torque arm 10 is detected by the load cell 11. A torque transmitted is increased in response to the increase of cure rate with time. A change of the torque can be detected by the load cell 11.

However, the viscoelasticity measuring apparatus of the prior art has a rotary motion mechanism of the type in which the vibration shaft 4 is vibrated by the motor 8 through the eccentric shaft 7 and the crank arm 6 connected thereto in order to realize the periodical vibration of the driving dice 2. Accordingly, a periodical vibration with a predetermined period and a predetermined amplitude can be imparted to the driving dice 2, but the apparatus has a disadvantage in that a reciprocal vibration does not have a sinusoidal waveform.

Asymmetry of such a reciprocal vibration will be described with reference to FIG. 1B. Reference numeral 26 denotes the junction between the crank arm 6 and the eccentric shaft 7 which is rotated by the motor 8 and reference numeral 27 denotes the junction between the crank arms 6A and 6B. A phase error and the asymmetry of the operation of this mechanism with respect to a sinusoidal waveform can be simply explained in terms of the positions 26A and 26B of the junctions 26. That is, the positions 6A and 6B assumed by the connection on the drive shaft side correspond to the midpoint of the forward stroke and the backward stroke of the arm 4, respectively. If the arm 4 is driven in the sinusoidal waveform, the positions 6A and 6B of the connection on the drive shaft side would be symmetrical with respect to the drive shaft 1, so that their phase difference should be 180°.

However, as can be clearly seen in the figure, the aforesaid positional relation does not exist, and a phase error $\alpha$ is produced. The phase error $\alpha$ is equal to the oscillation amplitude angle (indicated by $\beta$ in the figure). To reduce the value of $\beta$ with respect to the same angle $\theta$, the lengh of the arm 6B has only to be increased as compared with those of the radius of rotation and the length of the arm 6A. However, since there is a spatial restriction to the actual system, it is usual practice to design the arms in a manner that the length of the arm 6A is substantially equal to the length of the arm 6B. As a result, the angle $\beta$ is substantially equal to the angle $\theta$. Consequently, in conversion mechanisms of the prior art, the drive waveform thus obtained can be said to be asymmetrical in that the phase error at the midpoint of its oscillation is substantially the same as the amplitude angle of the drive.

However, in the measuring apparatus of the type in which a torsional vibration with a predetermined amplitude angle is imparted to a viscoelastic material to obtain dynamic viscoelastic properties such as storage modulus, loss modulus, phase angle and so on based upon an exact relationship between the resulting torque waveform and the vibration waveform, data analysis is made on the assumption that the vibration waveform is exactly sinusoidal. In this case, it is especially preferable that the sinusoidal waveform is symmetrical without any distortion. As described above, however, the apparatus of the prior art cannot produce such an ideal waveform.

In the apparatus in which a viscoelastic specimen is used, the symmetry of distorted waveforms is very important. The reason is as follows. When a vibration of a periodical sinusoidal waveform with a predetermined period and a predetermined amplitude such as torsional angle strain is being imparted to such a viscoelastic material, the resulting vibration stress (for instance, torque) is represented as shown in FIG. 2.

In FIG. 2, $|M^*|$ is an amplitude of torque. $M_A$ is a magnitude of torque when an angular waveform $S_A$ assumes a maximum (to be referred to as "elastic component of torque"). $M_B$ is a magnitude of torque when an angular waveform $S_A$ assumes zero in phase (to be referred to as "viscosity component of torque" or "loss torque"). $\delta$ is a difference in phase between the torque waveform $S_B$ and the angular waveform $S_A$ and is referred to as "phase angle or loss angle".

The above-described terms $|M^*|$, $M_A$, $M_B$ and $\delta$ satisfy the following equations (1) and (2). In order that these equations (1) and (2) are satisfied, the angular waveform $S_A$ must be an exactly sinusoidal waveform without any distortion.

$$|M^*| = \sqrt{M_A^2 + M_B^2} \quad (1)$$

$$\tan \delta = M_B/M_A \quad (2)$$

The loss torque $M_B$ is a torque produced when the angular waveform $S_B$ passes the midpoint, so that when the midpoint does not coincide with the phase 0°, 180° or 360°, the loss torque $M_B$ contains an error corresponding to such a difference of phase.

Especially, when vulcanization of rubber is made the loss angle $\delta$ after vulcanization is extremely small. For instance, the loss torque $M_B$ is about 1/10–1/1000 of the torque amplitude $|M^*|$. Accordingly, the error of the loss torque $M_B$ cannot be relatively decreased, unless the error due to the asymmetry of the waveform is extremely small at the midpoint of the angular waveform $S_A$.

This is the reason why an exactly sinusoidal waveform must used as the angular waveform in a viscoelasticity measuring apparatus, especially for rubber material, when $\tan \delta$ or $M_B$ is obtained.

Furthermore, in a viscoelasticity measuring apparatus of the prior art, a time required for measuring one specimen is of the order of a few minutes at most in most cases. Therefore, if a loading of a specimen and a removal of a tested specimen are carried out manually, there is a problem in rationalizing process control.

In order to solve the above and other problems, there has been proposed to use a robot to load a specimen in an apparatus and to remove a tested specimen therefrom. In such a case, it is required that the robot accomplishes a step of receiving a specimen at a predetermined reception position and transporting it to a dice at a measurement position and a step of removing a tested specimen from the measurement position. In such a case, if the robot advances to and retreats from the measurement position sequentially every time that a specimen is loaded or removed, a relatively long time is required, so that it becomes useless to use the robot. Furthermore, in a viscoelasticity measuring apparatus of the prior art, a tested specimen is attached to the upper or lower dice at random, so that it is difficult to use the robot.

SUMMARY OF THE INVENTION

One of the objects of the present invention is, therefore, to provide a viscoelasticity measuring apparatus in which the rotary movement of a drive shaft is converted to the rotary vibratory movement of a driven shaft that has correct symmetry and high approximation to a sinusoidal wave, so that such a sinusoidal waveform is imparted as a torsional vibration to a specimen through a driving dice to obtain measurement data with a minimum error.

Another object of the present invention is to provide a viscoelasticity measuring apparatus in which an automatic handling apparatus such as a robot can load a specimen and remove it in a simple manner so that the above-described problem can be solved.

In order to achieve the above objects, a dynamic viscoelasticity measuring apparatus of torsional vibration type according to the present invention comprises a driving portion for converting a rotary movement to a rotary vibratory movement having a driving shaft having an eccentric end for rotation at an isometric velocity, a driven shaft supported at a right angle to the driving shaft for rotation, an intermediate arm revolving along the side of a cone having a top at the point of intersection of the center line of the driving shaft and the center line of the driven shaft disposed at right angles to each other and a bottom at a circle described by the eccentric end of the driving shaft, and connecting means for operatively connecting opposite ends of the intermediate arm to the driven shaft and the driving shaft; and a driving dice for imparting vibration to a specimen, dynamic viscoelasticity of which is to be measured, through the swinging shaft, the vibration having an approximately sinusoidal waveform with complete symmetry.

Here, the connecting means for operatively connecting the one end to the driven shaft may comprise a plate spring for connecting the driven shaft to the intermediate arm, and the plate spring extends along a plane transverse to the driven shaft center line.

In a second aspect of the present invention, a dynamic viscoelasticity measuring apparatus of torsional vibration type comprises a lower dice having a driving dice for imparting swinging vibration to a specimen, dynamic viscoelasticity of which is to be measured, through a swinging shaft and a stationary dice so disposed as to surround the driving dice; an upper dice having a detection dice which is opposed to the driving dice to define a specimen chamber together with the driving dice so that a vibration is obtained from the specimen filled in the specimen chamber and a stationary dice so disposed as to surround the detection dice; and a driving portion for driving the driving dice, the portion having a driving means, an intermediate arm having one end which is eccentrically, movably and pivotably attached to the driving shaft of the driving means so that the intermediate arm rotates along the conical surface of a cone having an apex coinciding with the point of intersection between an axis perpendicular to the axis of the swinging shaft of the driving dice and the extension of the axis of the driving shaft of the driving means, and a connecting member which is interposed between the other end of the intermediate arm and the swinging shaft in such a way that the rotation of the swinging shaft is restricted and the freedom for changing the angle between the swinging shaft and the intermediate arm is permitted, so that the vibration has an approximately sinusoidal waveform with complete symmetry.

It is preferable that the diameter of the driving dice is larger than that of the detection dice. Here, the stationary dice of the upper dice may have an annular groove which is inclined relative to the lower surface of the stationary dice. The driving dice may have a larger diameter than the detection dice and the stationary dice of the upper dice may have an annular groove which is inclined relative to the lower surface of the stationary dice.

The driving dice may have an outer peripheral portion which is tapered and the stationary dice of the lower dice may have an inner peripheral portion which is tapered.

In a third aspect of the present invention, a dynamic viscoelasticity measuring apparatus of torsional vibration type comprises a lower dice having a driving dice for imparting swinging vibration to a specimen, dynamic viscoelasticity of which is to be measrued, through a swinging shaft and a stationary dice so disposed as to surround the driving dice; an upper dice having a detection dice which is opposed to the driving dice to define a specimen chamber together with the driving dice so that a vibration is obtained from the specimen filled in the specimen chamber and a stationary dice so disposed as to surround the detection dice; and an annular groove which is formed in the lower surface of the stationary dice of the upper dice which faces the specimen chamber in a manner that the annular groove is inclined relative to the lower surface of the stationary dice, so that the specimen is held by the upper dice at the annular groove after the specimen is cured.

It is preferable that the diameter of the driving dice is larger than that of the detection dice. The driving dice may have an outer peripheral portion which is tapered and the stationary dice of the lower dice may have an inner peripheral portion which is tapered.

In a fourth aspect of the present invention, a dynamic viscoelasticity measuring apparatus of torsional vibration type comprises a lower dice having a driving dice for imparting swinging vibration to a specimen, dynamic viscoelasticity of which is to be measrued, through a swinging shaft and a stationary dice so disposed as to surround the driving dice; an upper dice having a detection dice which is opposed to the driving dice to define a specimen chamber together with the driving dice so that a vibration is obtained from the specimen filled in the specimen chamber and a stationary dice so disposed as to surround the detection dice; and a specimen receiving groove formed in the stationary dice of the lower dice to surround the specimen chamber and for receiving a part of the specimen overflowed from the specimen chamber.

Here, the dynamic viscoelasticity measuring apparatus of torsional vibration type may further comprise an annular groove which is formed in the lower surface of the stationary dice of the upper dice which faces the specimen chamber in a manner that the annular groove is inclined relative to the lower surface of the stationary dice, so that the specimen is held by the upper dice at the annular groove after the specimen is cured. Here, the dynamic viscoelasticity measuring apparatus may further comprise a communicating groove for communicating the specimen chamber with the specimen receiving groove to guide the specimen overflowed from the specimen chamber into the specimen receiving groove, so that a part of the overflowed specimen is held by the burr holding members.

The dynamic viscoelasticity measuring apparatus of torsional vibration type may further comprise at least one pair of burr holding members which are attached to the stationary dice of the upper dice and disposed radially outside of the annular groove in manner that the burr holding members are inserted into the specimen receiving groove, so that a part of a specimen overflowed from the specimen chamber are accepted by the burr holding members.

The diameter of the driving dice may be larger than that of the detection dice. The driving dice may have an outer peripheral portion which is tapered and the stationary dice of the lower dice may have an inner peripheral portion which is tapered.

BRIEF DESCRIPTION OF THE DRAWINGS

FIG. 8A is a bottom view showing an upper detection dice and a stationary dice;

FIG. 8B is a top view showing a lower driving dice and a stationary dice;

FIG. 8C is a sectional view taken along the line X—X in FIG. 8B;

FIG. 11A is a sectional view showing a specimen mounted on an upper dice;

FIG. 11B is a bottom view showing the specimen mounted on an upper dice;

DETAILED DESCRIPTION OF THE PREFERRED EMBODIMENTS

The present invention will now be explained in detail with reference to the accompanying drawings.

Figure 3:
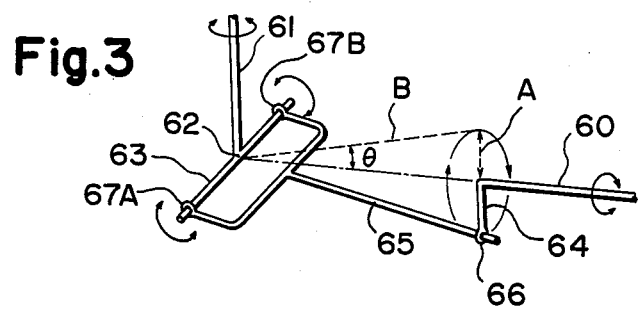
FIG. 3 is a schematic view illustrating an underlying principle of a mechanism for imparting a sinusoidal vibration or swinging motion to a specimen in a viscoelasticity measuring apparatus in accordance with the present invention.

FIG. 3 is a schematic view used to explain an underlying principle of a driving mechanism capable of imparting a symmetrical sinusoidal waveform to a driving dice in a viscoelasticity measuring apparatus in accordance with the present invention.

A driving shaft 60 and a driven shaft 61 are so arranged that their axes intersect each other at a point 62 at a right angle with respect to each other. To facilitate explanation, it is defined that the driven shaft 61 is extended vertically, while the driving shaft 60 is extended horizontally. A rigid and straight arm 63 is extended horizontally from the lower end of the driven shaft 61 and a rigid and straight arm 64 is extended vertically from one end of the driving shaft 60. The arms 63 and 64 are interconnected to each other by a yoke-like intermediate lever 65. The arm 64 is connected to the driving shaft 60 at the forward end thereof at a right angle thereto. The lever 65 and the arm 64 are connected to each other at a joint 66. The junction 66 is rotatable and bendable in such a way that the lever 65 can rotate about the axis of the driving shaft 60 with the point 62 being a pivotal point.

The arm 63 and the bifurcated ends 67A and 67B of the lever 65 are joined to each other in such a way that the lever 65 can rotate about the axis of the arm 63.

Assume that the arm 64 has an effective length A which is the radius of rotation of the joint 66 about the driving shaft 60. The intermediate lever 65 has an effective length B which is equal to the distance between the crossing 62 and the joint 66. As the driving shaft 60 rotates, the center line of the intermediate lever 65 will revolve along the side of a cone having a bottom at a circle described by the joint 66 and a top at the point of intersection 62. The motion of the intermediate lever 65 is transmitted to the driven shaft 61 via the joints 67A and 67B and the arm 63. In this case, since the vertical component of the movement of the intermediate lever 65 is absorbed by its idle rotation of the intermediate lever 65 about the joints 67A and 67B, only the horizontal component thereof is transmitted to the driven shaft 61.

That is, a rotary vibration having an amplitude angle which is ½ the vertical angle (the angle $\theta$ in FIG. 3) of the aforesaid cone is imparted to the driven shaft 61. As can be clearly seen in FIG. 3, the relation $A/B = \sin \theta$ is satisfied among the length A of the arm 64, the length B of the intermediate lever 65 and the vertical angle (½) $\theta$ of the cone.

If the driving shaft 60 is rotated at a constant rotational speed by a motor (not shown) directly or through a reduction gear (not shown), then the joint 66 is caused to move in circular motion at a constant angular velocity and the horizontal component of the circular motion of the arm 64 vibrates with an approximately sinusoidal waveform with time. As a result, the vibrating motion of the driven shaft 61 describes an approximate sinusoidal waveform with a complete symmetry.

An amplitude ratio of the approximately sinusoidal waveform obtained in this way to an exactly sinusoidal waveform is 1 at the midpoint of the amplitude and maximized at both ends of the amplitude. The maximum value is equal to the ratio of tan $\theta$ and $\theta$. As a result, a good approximate relation can be obtained, so long as $\theta$ is not so large in value, and when $\theta$ has a very small value, a very high approximation can be achieved.

Some examples will be described. When the values 0.175, 0.052 and 0.0175 radians (or 10, 3 and 1 degrees, respectively) were selected for $\theta$, the aforesaid ratios were 1.010, 1.0009 and 1.0001, respectively, which were very close to unity. It should be noted that the symmetry of the waveform has no relation with the angle $\theta$. Thus, the driven shaft 61 vibrates while describing an accurate sinusoidal waveform with complete symmetry at all times, so that a phase error due to asymmetry can be maintained at zero throughout the entire motion of the driven shaft 61.

Figure 4:
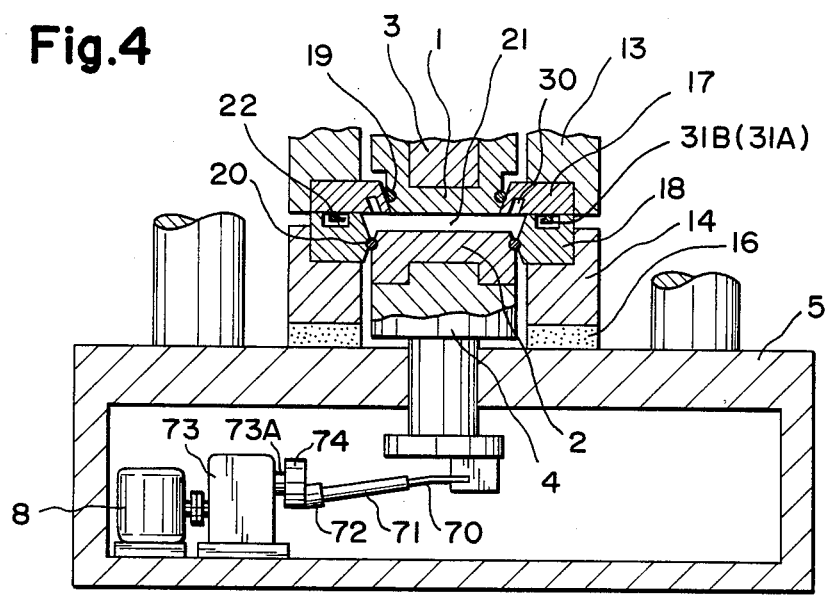
FIG. 4 is a sectional view showing one embodiment of the sinusoidal vibration imparting mechanism.

FIG. 4 shows one embodiment of a mechanism for imparting a vibration having the above-described approximately sinusoidal waveform with symmetry to the driving dice 2. The swinging shaft 4 is supported by the lower base 5 so as to be swingable about the axis of the shaft 4. One end of a plate spring 70 is connected to the lower end of the swinging shaft 4 while the other end of the plate spring 70 is connected to an intermediate arm 71 which in turn is supported rotatably and swingably by means of a bearing 72. The connections of the plate spring 70 to the shaft 4 and the arm 71 can be made by any known method that can withstand the drive torque, such as threading, brazing, welding, etc.

Figure 1A:
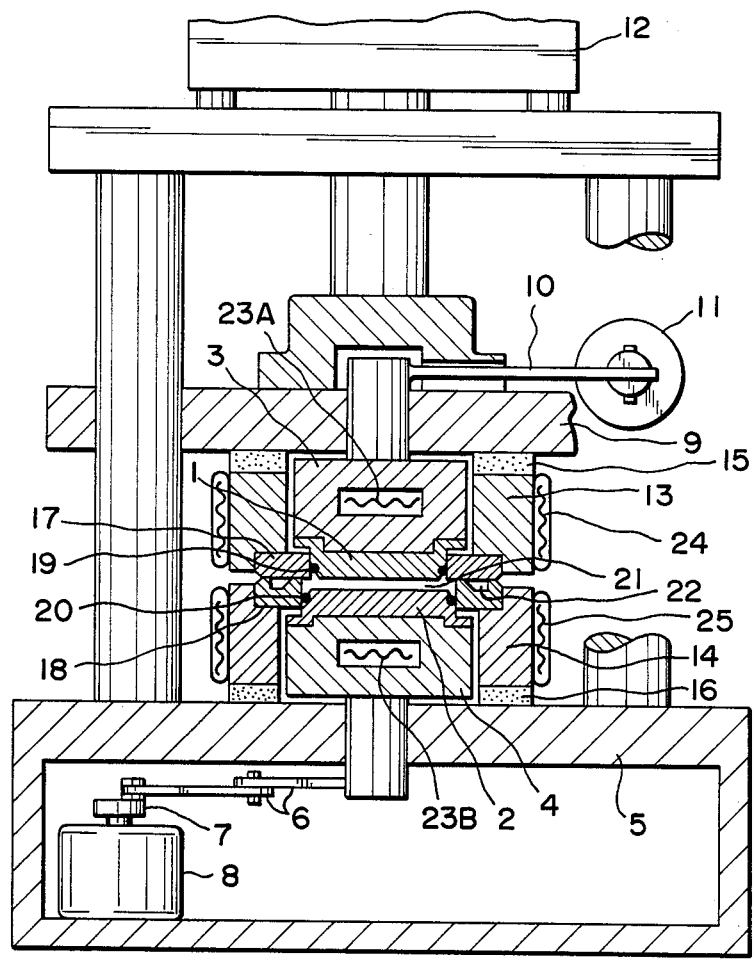
FIG. 1A is a sectional view showing a viscoelasticity measuring apparatus of prior art.
Figure 1B:
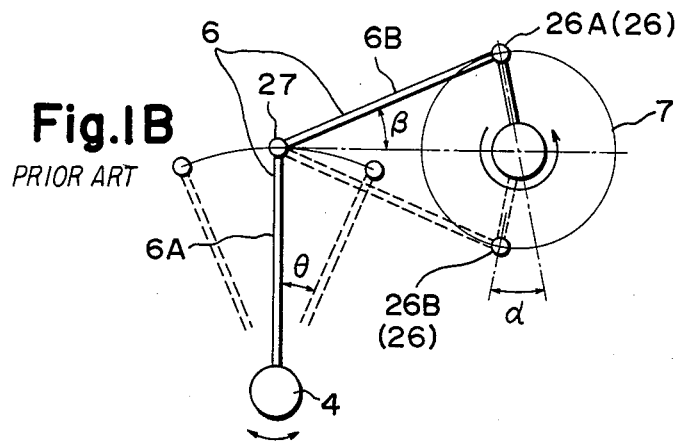
FIG. 1B is a schematic view used to explain that the distorted waveform produced by the viscoelasticity measuring apparatus as shown in FIG. 1A does not have a sinusoidal waveform.
Figure 2:
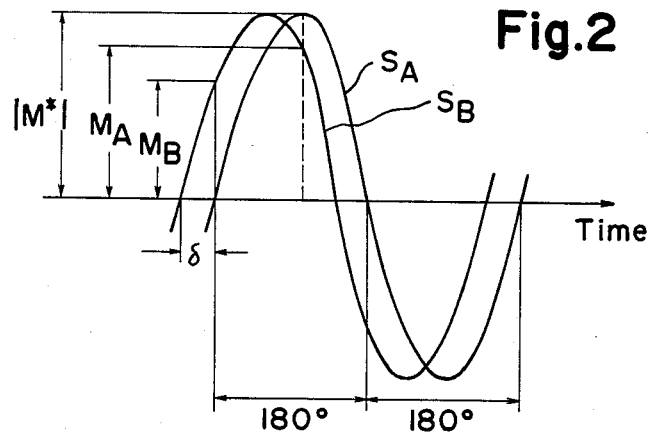
FIG. 2 illustrates a waveform used to explain the relations of the viscoelasticity terms of a specimen when a distortion waveform imparted to the specimen is a sinusoidal wave.

The use of a plate spring eliminates play in the connection between the driven shaft and the intermediate arm, so that rotational vibration of a low amplitude and high precision can be advantageously given. The embodiment shown in FIG. 4 offers the additional advantages that the construction is greatly simplified and the cost is greatly reduced as compared with the mechanism of the prior art as shown in FIG. 1A.

The bearing 72 is preferably in the form of an automatic self-aligning radial bearing, spherical roller bearing, spherical slide bearing or other spherical type bearing, since it requires latitude in rotation and bending. Since a spherical slide bearing has a large allowable bending angle during rotation, it can be used with a large amplitude angle. When the drive torque is low, a pivot type bearing may be used as the bearing 72.

A reduction gear 73 is connected to the motor 8 and a rotary disc 74 is carried by the output shaft 73A of the reduction gear 73. The bearing 72 is mounted at an eccentric position of the disc 74. Upon rotation of the output shaft 73A, the intermediate arm 71 rotates along the conical surface of cone and the vertical component of the motion of the intermediate arm 71 is absorbed by the plate spring 70, so that the swinging movement is imparted to the swinging shaft 4 in such a way that the swinging shaft 4 describes an approximately sinusoidal waveform which is symmetrical about the axis thereof.

Figure 5:
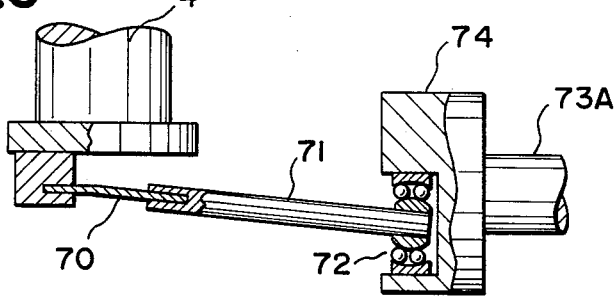
FIG. 5 is an elevational view showing the details of the mechanism shown in FIG. 4.
Figure 6:
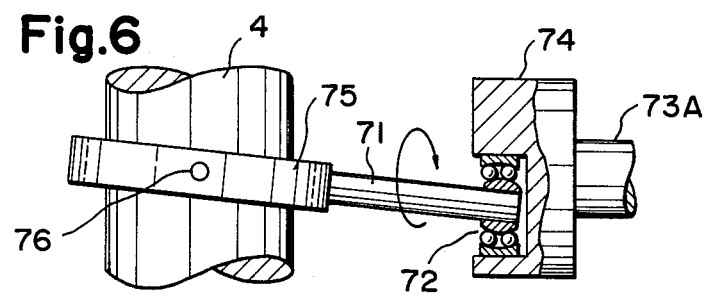
FIG. 6 is an elevational view showing in detail another embodiment of the mechanism.

In a modification as shown in FIG. 6, a ring member 75 and pins 76 are used instead of the plate spring 70 as shown in FIG. 5. That is, the ring member 75 is pivoted to the swinging shaft 4 via the horizontal pins 76. The vertical component of the movement of the intermediate arm 71 is absorbed by the pivot pins 76, so that the same function as described above with reference to FIG. 5 can be attained.

Next, another embodiment of the present invention will be described.

The second embodiment is adapted for use with a robot which inserts a specimen into a specimen chamber and removes it therefrom. It is ensured that positive and simple operations of the robot are realized.

Figure 7:
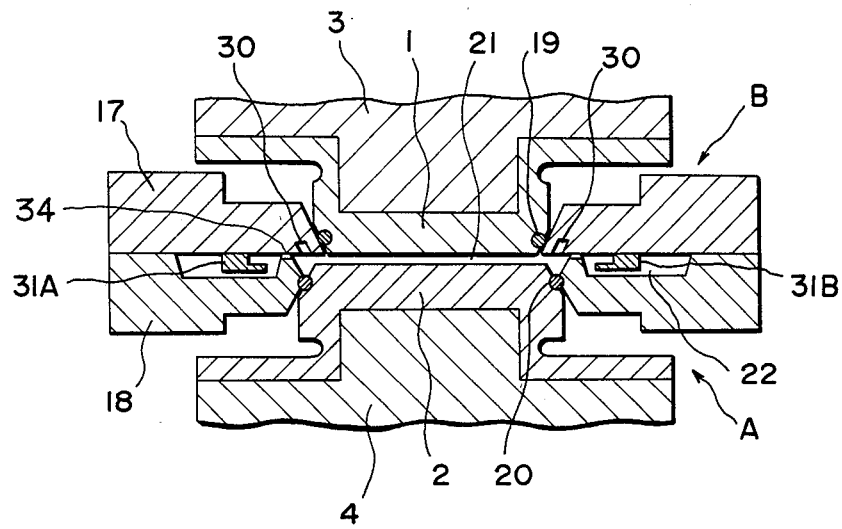
FIG. 7 is a sectional view showing one embodiment of a construction of a specimen chamber in a viscoelasticity measuring apparatus in accordance with the present invention.

Referring now to FIG. 7, a lower dice A comprises the driving dice 2 and the stationary dice 18 and an upper dice B comprises the detection dice 1 and the stationary dice 17. In the second embodiment, the stationary dice 17 of the upper dice B has an annular and inclined groove 30 on the side facing the specimen chamber 21.

Furthermore, as shown also in FIG. 8A, burr holding members 31A and 31B having an L-shaped cross sectional configuration are disposed in a symmetrical manner with respect to the axis of the shaft 3 and are radially outwardly spaced apart from the inclined groove 30 in such a way that the burr holding members 31A and 31B are opposed to and contained in a burr groove 22. Reference numeral 32 denotes a grating-like cross groove which consists of a plurality of vertical and horizontal grooves and which is formed on the surface of the detection dice 1. Because of the cross groove 32, a specimen is prevented from being slipped when the driving dice 2 imparts a twisting vibration to it.

FIGS. 8B and 8C show the construction of the lower dice A. The upper surface of the driving dice 2 of the lower dice A which defines the specimen chamber 21 is formed with a cross groove 33 which is substantially similar in construction to the above-described grating-like cross groove 32. In order to facilitate the introduction of burr of the specimen into the burr groove 22 formed in the stationary dice 18, grooves 34 which communicates the groove 22 to the specimen chamber 21 are formed at circumferential positions in opposed relationship with the burr holding members 31A and 31B.

Figure 9A:
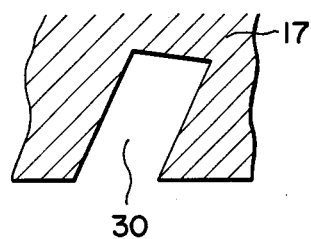
FIGS. 9A–9C are sectional views showing inclined grooves formed in the upper dice of the viscoelasticity measuring apparatus in accordance with the present invention.
Figure 9B:
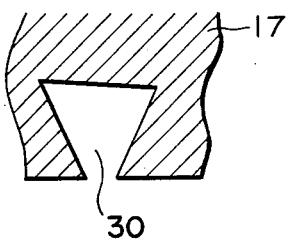
Figure 9C:
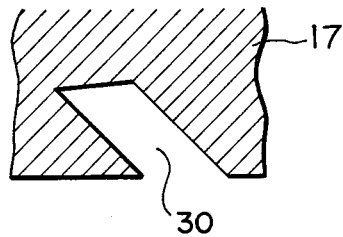

FIGS. 9A–9C show in cross section various types of the inclined grooves 30 formed in the upper dice B. A part of the specimen is introduced into the inclined groove 30 while the specimen is pressed, so that when the upper dice B is lifted after the measurement, the specimen can always be securely held on the side of the upper dice B.

Therefore, it is preferable that the angle between the inclined walls of the groove 30 and the horizontal surface of the dice is in the range of 30° through 85° and it is more preferable that the angle is in the range of 40° through 70°. In the present invention, the cross sectional configuration is not limited to that as shown in FIG. 9A. For instance, the groove 30 may have an inverted-wedge-shaped cross sectional configuration as shown in FIG. 9B, or the groove 30 may be inclined in the opposite direction as shown in FIG. 9C. The groove 30 may have any cross sectional configuration as long as the following requirements are met. That is, a part of the specimen is easily introduced into the groove 30 during pressing the specimen. When the upper dice B is lifted, the specimen is also lifted in contact with the lower surface of the upper dice B. The specimen can be readily removed by removing means of a robot hand to be described below.

Figure 10B:
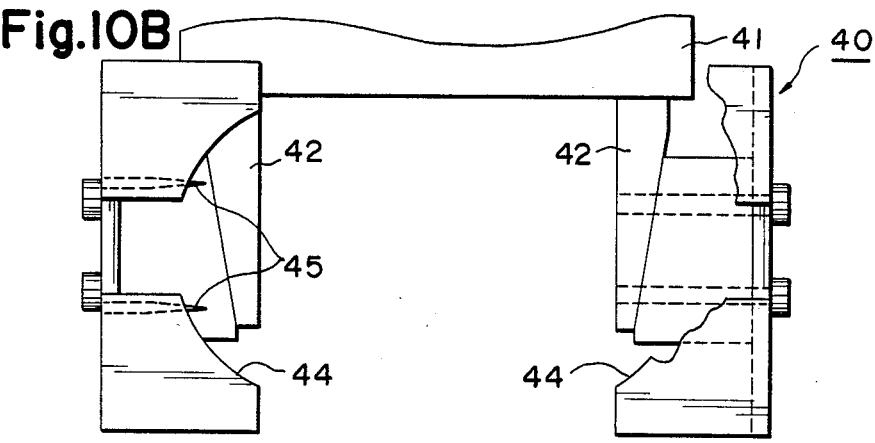
FIG. 10B is a top view showing the robot hand to be used in the present invention.
Figure 10A:
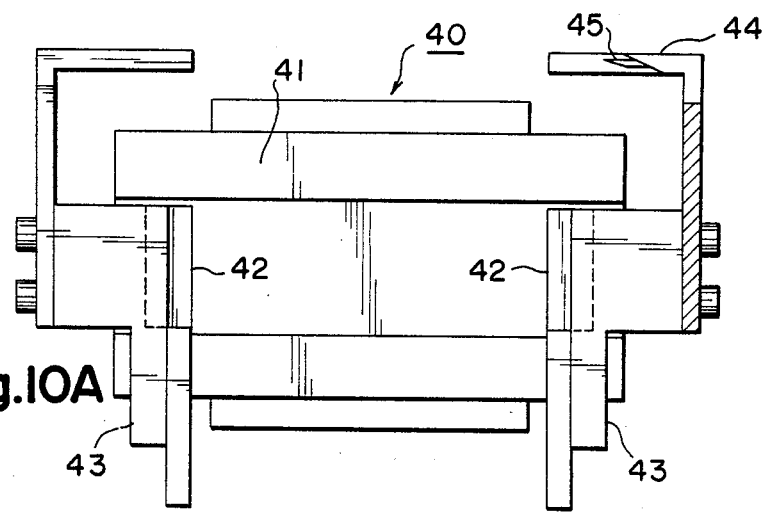
FIG. 10A is a side view showing a robot hand to be used in the present invention.
Figure 10C:
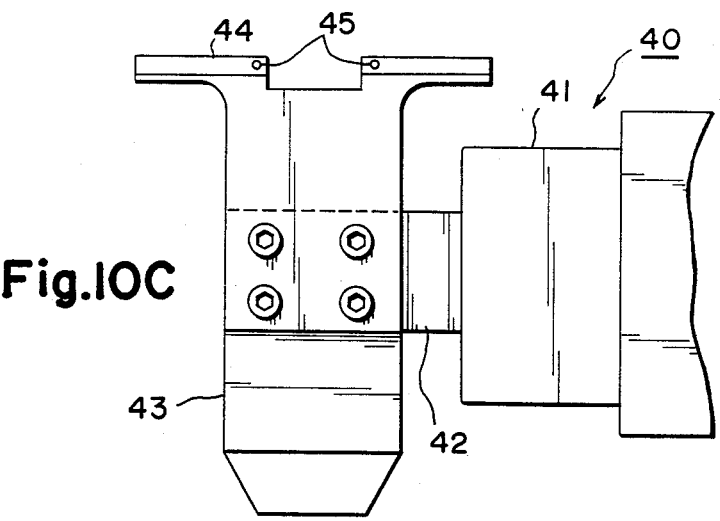
FIG. 10C is a side view showing the robot hand to be used in the present invention.

FIGS. 10A–10C show one embodiment of a robot hand used to insert a specimen into the specimen chamber 21 and remove it therefrom. Reference numeral 40 denotes a robot hand comprising an arm 41 which can be bent, rotated, expanded and contracted, a pair of rods 42 which are attached to the leading end of the arm 41 and which are movable toward or away from each other, clamping plates 43 disposed in opposed relationship with the pair of rods 42, respectively, and scraping edges 44 which are disposed on the clamping plates 43 in opposed relationship with each other. Reference numeral 45 denotes fork-members which are extended further from the scraping edges 44. The pair of fork-members 45 are penetrated into a specimen so that the specimen can be securely held in position or easily removed.

The robot hand 40 with the above-described construction accomplishes the operations to be described below in accordance with a predetermined sequence program.

FIGS. 11A and 11B show a measured specimen attached to the lower surface of the dice B shown in FIG. 7 when the upper dice B is lifted.

More particularly, a specimen 50 which is pressed in the specimen chamber 21 is forced into the inclined groove 30 formed in the upper stationary dice 17. At the same time, the specimen 50 is drawn from the specimen chamber 21 toward the burr groove 22 and a part of the specimen 50 which is drawn in the direction of the holding members 31A and 31B through the groove 34 is also charged into the recessed portions of the members 31A and 31B.

Both ends of the specimen 50 are firmly held by the holding members 31A and 31B and further by the inclined groove 30, so that the specimen 50 can be securely attached to the lower surface of the dice B.

Next, the operation of removing the specimen 50 which has been measured and which is attached to the lower surface of the dice B by the above-described robot hand 40 and the operation of placing a new specimen upon the upper surface of the lower dice A will be carried out in accordance with the following step:

(1) While a preceding specimen is being measured, a pair of the clamping plates 43 clamps a specimen placed over a specimen table (not shown).

(2) After the measurement is completed, the robot hand moves into a space formed between the dices A and B after the dices A and B are vertically moved away from each other and then the robot hand discharges to place a specimen over the driving dice 2 of the evacuated dice A.

Figure 12A:
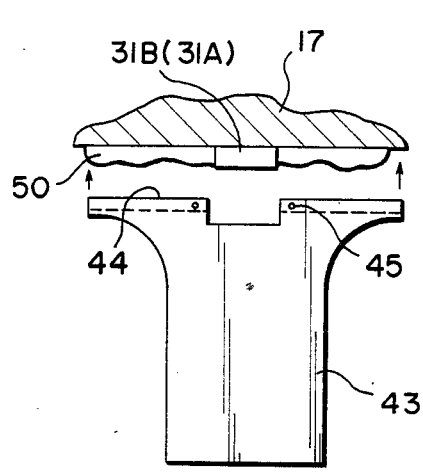
FIGS. 12A and 12B are side views used to explain the operation for removing a specimen mounted on the upper dice by the robot hand.
Figure 12B:
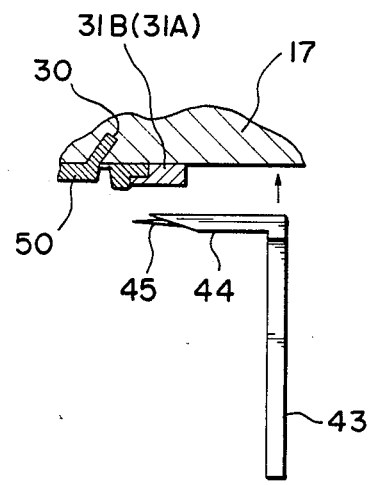
Figure 12C:
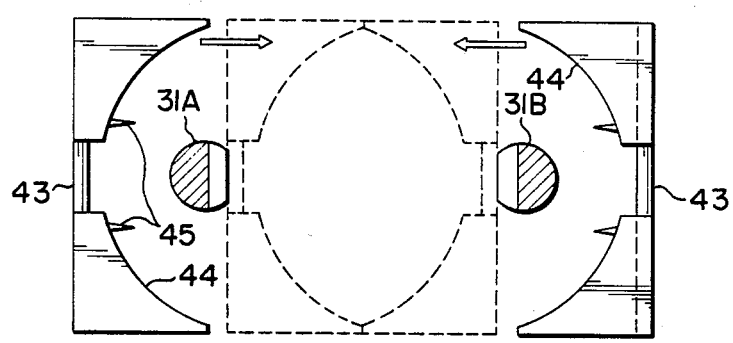
FIG. 12C is a top view corresponding to FIGS. 12A and FIG. 12B.

(3) Thereafter, as shown in FIGS. 12A and 12B, the clamping plates 43 and the scraping edges 44 are lifted and then the scraping edges 44 are moved toward each other as shown in FIG. 12C at a level substantially equal to the horizontal lower surface of the dice B, so that the measured specimen 50 attached to the dice B is scraped off and held by the robot hand.

(4) The robot hand is retracted away from the specimen chamber and dumps the retracted specimen into a dumping area.

As described above, when one specimen-replacement operation is carried out, it is not necessary for the robot hand to repeatedly move the same path. That is, it is sufficient that the robot hand makes only one reciprocal motion relative to the measuring portion. The specimens can be treated smoothly within a short period of time by a series of sequential operations of the robot hand. As a result, the cure test can be carried out with a very high efficiency.

It is to be understood that a specimen handling robot to be used in the present invention is not limited to the robot hand of the type described above and that any type of specimen handling robot hand capable of loading a specimen and removing it after the test may be used as a matter of course.

So far it has been described that the upper stationary dice 17 is formed with the inclined groove 30. In addition to the groove 30, it is also preferable that the lower dice A is so designed and constructed that a measured or tested specimen may be easily removed or separated from the lower dice A. To this end, for instance, it is preferable that, as shown in FIG. 8C, the inner side walls 60 of the stationary dice 18 which defines the side walls of the specimen chamber 21 are tapered upwardly. Furthermore, it is preferable that the outer side walls 61 of the driving dice 2 are also tapered upwardly and outwardly. Moreover, it is preferable that the inner and outer side walls 63 and 64 of the burr groove 22 are tapered upwardly and outwardly. It is also preferable that the surfaces of the driving dice 2 and lower stationary dice 18 which contact the specimen are formed with a releasing coating which facilitates the separation of a specimen. Such coating is, for instance, a fluoro coating like PTFE. It is also preferable that the above-described manners are employed in combination.

In the embodiments described above, the diameter of the driving dice 2 is greater than that of the detection dice 1. If the detection and driving dices 1 and 2 have the same diameter, a specimen is easily influenced by adverse effects due to complicated distortions produced around the periphery of the driving dice 2. As a result, data errors tend to occur very frequently. With this in view, it is also preferable that the diameter of the driving dice 2 is greater than that of the detection dice 1. The adverse effects produced around the periphery of the driving dice 2 are kinds of edge effects. According to the present invention such adverse effects can be substantially eliminated.

As described above, according to the present invention, the driving apparatus in the dynamic viscoelasticity measuring apparatus of torsional vibration type which imparts swinging vibration to the driving dice comprises a driving source, an intermediate arm whose one end is rotatably and pivotably supported by the driving shaft which is arranged essentially to the driving source and which rotates along the conical surface of a cone whose apex coincides with the point of intersection between an axis perpendicular to the axis of the swinging shaft of the driving dice and the extension of the axis of the driving shaft, and a joint member which is interposed between the other end of the intermediate arm and the swinging shaft and which restricts the movement in the direction of rotation of the swinging shaft and which gives freedom to the angle between the swinging shaft and the intermediate arm. As a result, a vibration having an approximately sinusoidal waveform which has a high accuracy of sinusoidal waveform and complete symmetry is imparted to a specimen. Therefore, viscoelasticity torque can be measured with a higher degree of accuracy without including phase difference to be caused by the asymmetry.

The lower surface of the stationary dice of the upper dice which faces the specimen chamber is formed with an annular and inclined groove. Into at least one pair of the burr holding members is introduced a part of a specimen emerging from the specimen chamber when the specimen is pressed and there are provided grooves for guiding the specimen emerged from the specimen chamber toward the burr holding members. The side walls of all the grooves formed in the upper surface of the lower dice are tapered upwardly. As a result, when the upper dice is lifted, the measured specimen can be securely attached to the upper dice by the annular and inclined groove and the burr holding members. By a sequence of simple operations of a robot hand or the like, a new specimen can be placed on the driving dice very smoothly within a short period of time and the measured specimen which is always attached to the lower surface of the upper dice can be easily scraped off and removed. Thus, the present invention promotes automation of measuring process.

What is claimed is:

1. A dynamic viscoelasticity measuring apparatus of torsional vibration type comprising:
    a driving portion for converting a rotary movement to a rotary vibratory movement having
        a driving shaft having an eccentric end for rotation at an isometric velocity,
        a driven shaft supported at a right angle to said driving shaft for rotation,
        an intermediate arm revolving along the side of a cone having a top at the point of intersection of the center line of said driving shaft and the center line of said driven shaft disposed at right angles to each other and a bottom at a circle described by the eccentric end of the driving shaft, and
        connecting means for operatively connecting opposite ends of said intermediate arm to said driven shaft and said driving shaft; and
    a driving dice for imparting vibration to a specimen, dynamic viscoelasticity of which is to be measured, through said driving shaft, said vibration having an approximately sinusoidal waveform with complete symmetry.

2. A dynamic viscoelasticity measuring apparatus of torsional vibration type as claimed in claim 1, wherein said connecting means comprises a plate spring for connecting said driven shaft to said intermediate arm, said plate spring extending along a plane transverse to said center line of said driven shaft.

3. A dynamic viscoelasticity measuring apparatus of torsional vibration type comprising:
    a lower dice having a driving dice for imparting swinging vibration to a specimen, dynamic viscoelasticity of which is to be measured, through a swinging shaft and a stationary dice so disposed as to surround said driving dice;
    an upper dice having a detection dice which is opposed to said driving dice to define a specimen chamber together with said driving dice so that a vibration is obtained from said specimen filled in said specimen chamber and a stationary dice so disposed as to surround said detection dice; and
    a driving portion for driving said driving dice, said portion having a driving means, an intermediate arm having one end which is eccentrically, movably and pivotably attached to the driving shaft of said driving means so that said intermediate arm rotates along the conical surface of a cone having an apex coinciding with the point of intersection between an axis perpendicular to the axis of said swinging shaft of said driving dice and the extension of the axis of said driving shaft of said driving means, and a connecting member which is interposed between the other end of said intermediate arm and said swinging shaft in such a way that the rotation of said swinging shaft is restricted and the freedom for changing the angle between said swinging shaft and said intermediate arm is permitted, so that said vibration has an approximately sinusoidal waveform with complete symmetry.

4. A dynamic viscoelasticity measuring apparatus of torsional vibration type as claimed in claim 3, wherein the diameter of said driving dice is larger than that of said detection dice.

5. A dynamic viscoelasticity measuring apparatus of torsional vibration type as claimed in claim 3, wherein said stationary dice of said upper dice has an annular groove which is inclined relative to the lower surface of said stationary dice.

6. A dynamic viscoelasticity measuring apparatus of torsional vibration type as claimed in claim 3, wherein said driving dice has a larger diameter than said detection dice and said stationary dice of said upper dice has an annular groove which is inclined relative to the lower surface of said stationary dice.

7. A dynamic viscoelasticity measuring apparatus of torsional vibration type as claimed in claim 3, wherein said driving dice has an outer peripheral portion which is tapered and said stationary dice of said lower dice has an inner peripheral portion which is tapered.

8. A dynamic viscoelasticity measuring apparatus of torsional vibration type comprising:
   a lower dice having a driving dice for imparting swinging vibration to a specimen, dynamic viscoelasticity of which is to be measured, through a swinging shaft and a stationary dice so disposed as to surround said driving dice;
   an upper dice having a detection dice which is opposed to said driving dice to define a specimen chamber together with said driving dice so that a vibration is obtained from said specimen filled in said specimen chamber and a stationary dice so disposed as to surround said detection dice;
   a specimen receiving groove formed in said stationary dice of said lower dice to surround said specimen chamber and for receiving a part of said specimen overflowed from said specimen chamber; and
   at least one pair of burr holding members which are attached to said stationary dice to said upper dice and disposed radially outside of said annular groove in a manner that said burr holding members are inserted into said specimen receiving groove, so that a part of a specimen overflowed from said specimen chamber are accepted by said burr holding members.

9. A dynamic viscoelasticity measuring apparatus of torsional vibration type as claimed in claim 8, further comprising:
   an annular groove which is formed in the lower surface of said stationary dice of said upper dice which faces said specimen chamber in a manner that said annular groove is inclined relative to said lower surface of said stationary dice, so that said specimen is held by said upper dice at said annular groove after said specimen is cured.

10. A dynamic viscoelasticity measuring apparatus of torsional vibration type as claimed in claim 9, further comprising:
    a communicating groove for communicating said specimen chamber with said specimen receiving groove to guide the specimen overflowed from said specimen chamber into said specimen receiving groove, so that a part of the overflowed specimen is held by said burr holding members.

11. A dynamic viscoelasticity measuring apparatus of torsional vibration type as claimed in claim 8, wherein the diameter of said driving dice is larger than that of said detection dice.

12. A dynamic viscoelasticity measuring apparatus of torsional vibration type as claimed in claim 8, wherein said driving dice has an outer peripheral portion which is tapered and said stationary dice of said lower dice has an inner peripheral portion which is tapered.

* * * * *